(12) United States Patent
Stone

(10) Patent No.: US 11,540,850 B1
(45) Date of Patent: Jan. 3, 2023

(54) DISPOSABLE TONGUE SCRAPER

(71) Applicant: Shamar Llwellyn Stone, Stone Mountain, GA (US)

(72) Inventor: Shamar Llwellyn Stone, Stone Mountain, GA (US)

( * ) Notice: Subject to any disclaimer, the term of this patent is extended or adjusted under 35 U.S.C. 154(b) by 156 days.

(21) Appl. No.: 17/207,923

(22) Filed: Mar. 22, 2021

Related U.S. Application Data

(60) Provisional application No. 63/132,371, filed on Dec. 30, 2020.

(51) Int. Cl.
| | |
|---|---|
| *A61B 17/24* | (2006.01) |
| *A61B 17/00* | (2006.01) |
| *A61B 17/32* | (2006.01) |

(52) U.S. Cl.
CPC .... *A61B 17/244* (2013.01); *A61B 2017/0042* (2013.01); *A61B 2017/00946* (2013.01); *A61B 2017/320008* (2013.01)

(58) Field of Classification Search
CPC ....... A61B 17/24; A61B 17/244; A61B 17/50; A61B 2017/0042; A61B 2017/00946; A46B 15/0081; A46B 15/0055
See application file for complete search history.

(56) References Cited

U.S. PATENT DOCUMENTS

| | | | | |
|---|---|---|---|---|
| 5,569,278 | A  * | 10/1996 | Persad | A61B 17/244 |
| | | | | 606/161 |
| 9,888,938 | B1 * | 2/2018 | Schwimmer | A61B 17/24 |
| 2004/0134008 | A1 * | 7/2004 | Pham | A46B 15/0081 |
| | | | | 606/161 |
| 2017/0164727 | A1 * | 6/2017 | Thakkar | A61B 17/244 |

* cited by examiner

*Primary Examiner* — Katherine H Schwiker

(57) ABSTRACT

The present invention relates to a disposable tongue scraper which has a strong and simple structure, a durable and efficient operation, comparatively inexpensive to manufacture, and a novel combination and arrangement of parts comprising a scraper body that forms a curved shape after bending at an acute angle at a bending point for scraping operation, a pair of handle casings attached with the scraper body, and a storage tissue net attached to the bottom of the scraper body to store the scraped oral wastes and to absorb the oral fluid. The present invention aims to provide the tongue scraper not only utilized for scraping the coating from the tongue, but also for storing the scraped oral wastes and saliva wastes from the mouth to maintain hygiene.

2 Claims, 3 Drawing Sheets

DISPOSABLE TONGUE SCRAPER

FIELD OF THE INVENTION

The present invention relates primarily to an oral hygiene cleaning device and more particularly it relates to a disposable tongue scraper with a built-in storage tissue net to dispose of oral wastes and saliva wastes from the mouth after scraping operation.

BACKGROUND OF THE INVENTION

The tongue is a soft and delicate muscular organ in the mouth of most vertebrates, which manipulates food for mastication and is used in the act of swallowing. The tongue can be easily affected by the microorganisms such as food debris, desquamated epithelial cells, and bacteria that often form a visible tongue coating. This coating has been identified as a major factor contributing to bad breath, which can be managed by using a tongue cleaner or scraper. The tongue bacteria produce malodorous compounds and fatty acids and account for 80 to 90% of all cases of mouth-related bad breath. Also, several types of oral cancer mainly affect the tongue. Hence, oral hygiene has become one of the basic requirements to prevent harmful oral diseases and plaque buildup.

The tongue scrapers have been widely available in the market for decades. They come in many variations, shapes, and sizes; all with the basic utility of cleaning the tongue effectively to scrape any build-up on the tongue. Particularly, scraping the tongue is a quick and simple action to tackle bad breath. Typically, the conventional tongue scraping devices contain paper or plastic material like the scraper itself and perform only singular action i.e. scraping. The user sticks their tongue out and uses light pressure to run the scraper across the entire surface of the tongue. Afterward, the user commonly scrapes the oral bacteria debris into a facility to eject fluid waste into. More than often this facility is a bathroom or restroom sink.

The conventional tongue scraping devices only clean the tongue but do not have a facility to store the waste fluid from the tongue when scraping. The tongue scrapers available in the market have no way of storing the saliva from the user; typically the bathroom sink is what the user would use as a facility to dispose of the scraped saliva waste from the tongue. The tongue scraper manufacturing companies claim that they produce disposable tongue scraper which is intended to be used only once but does not provide any means of storing waste from the tongue.

Various prior arts have been disclosed describing the tongue scraper or tongue cleaner. The prior art document U.S. Pat. No. 4,582,059A describes a hygienic tongue scraping and massage instrument for freeing and removing pathogenic foreign matter entrapped in upper surfaces of the tongue comprises a pair of elongated handles and a generally square crossbar formed with a scraping edge and having opposite ends connected respectively to forward ends of the handles. The connections of the opposite ends with the forward ends establish corners so that the scraping edge extends continuously along the crossbar to intersect the corners.

Another prior art document U.S. Pat. No. 6,428,554B1 describes a dual-action tongue scraper providing either a hard scrape or a soft scrape of the tongue, as desired. A hard scraping surface and a soft scraping surface are formed along the edges of a strip of flexible material. A user bends the strip of a flexible material such that generally only one of the hard scraping surfaces and the soft scraping surface contacts the user's tongue at a given time during scraping.

Furthermore, prior art document US20090198262A1 related to a tongue scraper that is disposable and is adapted for prophylactic and/or therapeutic action for the oral cavity. The dental implement includes a tongue scraper, a dental floss, a toothpick, a toothbrush, or combinations thereof. The dental implement may include a strip having a longitudinal dimension that is longer than its traverse dimension.

Moreover, prior art document CN201157383Y describes a tongue scraper that adopts a low-cost metallic copper wire of a proper length and thickness, the metallic copper wire is bent downwards to become a reversed V-shape, the two lower ends are bent inwards to become small circular rings as handheld handles when cleaning, and the upper arc-shaped part is pressed into a thin sheet as the scraping sheet and is polished smooth to prevent scratching.

However, the above-mentioned conventional tongue scrapers are different concerning functional configuration & design and do not apparently describe nor are they specifically tailored toward a means of storing oral waste and saliva. They are differentiable from the present invention both in utility and design.

The aforesaid conventional tongue scrapers encounter various problems along with waste storage limitations. Hence, there is a significant need and void in the market for inventing an improved disposable tongue scraper with a unique design which allows user to scrape the coating formed on the tongue due to food debris, desquamated epithelial cells and bacteria; as well as to store the scraped oral wastes and absorb the saliva into a storage means.

SUMMARY OF THE INVENTION

The present invention relates to a disposable tongue scraper that addresses the needs which were not fulfilled by the conventional arts. The disposable tongue scraper of the present invention has unique and useful improvements. The main objective of the present invention is to provide a tongue scraper not only utilized for scraping the coating from the tongue, but also for storing the scraped oral wastes and saliva wastes from the mouth to maintain hygiene.

According to the present invention, the disposable tongue scraper having a strong and simple structure, a durable and efficient operation, comparatively inexpensive to manufacture, and a novel combination and arrangement of parts comprising a scraper body that forms a curved shape after bending at an acute angle at a bending point for a scraping operation, a pair of handle casings attached with the scraper body, and a built-in storage tissue net attached to the bottom of the scraper body to store the scraped oral wastes and to absorb the oral fluid.

The disposable tongue scraper of the present invention provides multifold benefits concerning oral health and hygiene, which are described in the following pages of specification.

BRIEF DESCRIPTION OF DRAWINGS

Other objects, advantages, and novel features of the invention will become apparent from the following detailed description of the present embodiment when taken in conjunction with the accompanying drawings. These figures are not intended to limit the scope of the present invention but rather illustrate certain attributes thereof.

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION OF THE INVENTION

The foregoing disclosure has broadly outlined the features and technical advantages of the present disclosure so that the description of the disclosure that follows may be better understood. It should be appreciated by those skilled in the art that the conception and specific embodiment disclosed may be readily utilized as a basis for modifying or designing other structures for carrying out the same purposes of the present disclosure. The novel features which are believed to be characteristic of the disclosure, both as to its organization and method of operation, together with further objects and advantages will be better understood from the following description.

Before explaining the present invention in detail, it is to be understood that the invention is not limited in its application to the details of the construction and arrangement of parts illustrated in the accompanying drawings. The invention is capable of other embodiments, as depicted in different figures as described above, and of being practiced or carried out in a variety of ways. It is to be understood that the phraseology and terminology employed herein are for description and not of limitation.

It is to be also understood that the term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also contain one or more other components.

Reference will now be made in detail to a presently preferred embodiment of the invention, an example of which is illustrated in the accompanying drawings.

The present invention discloses an improved disposable tongue scraper with a built-in disposal mechanism that includes storage means which is capable of storing the scraped oral waste as well as absorbing the oral fluid as shown in accompanying drawings.

Figure 1:
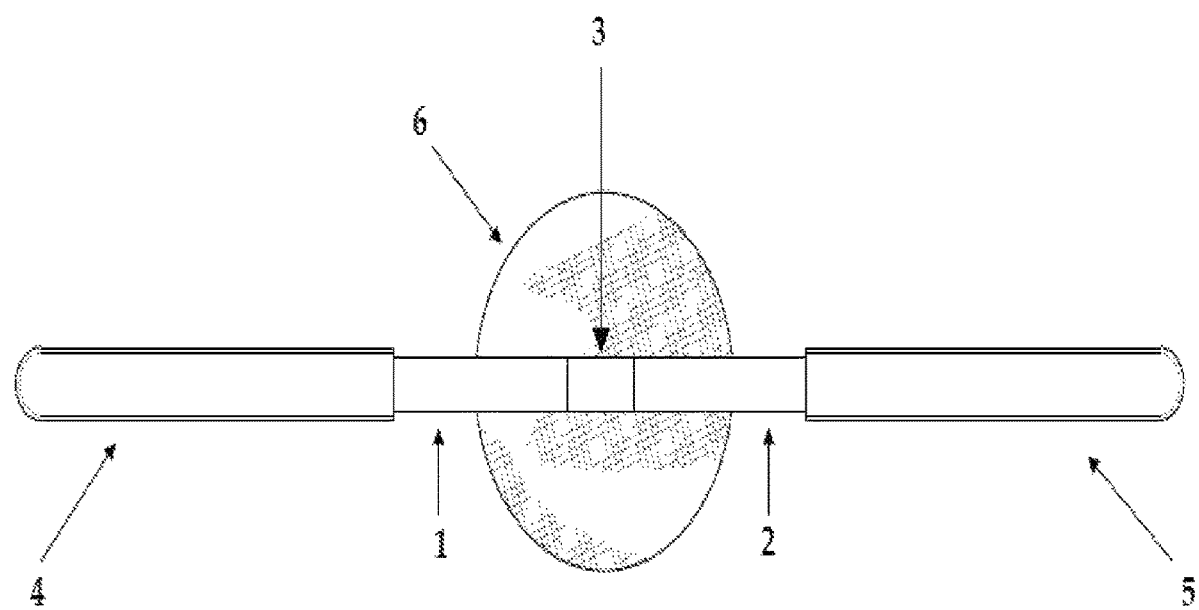
FIG. 1 illustrates a top view of an expanded disposable tongue scraper, according to an embodiment of the present invention.
Figure 2:
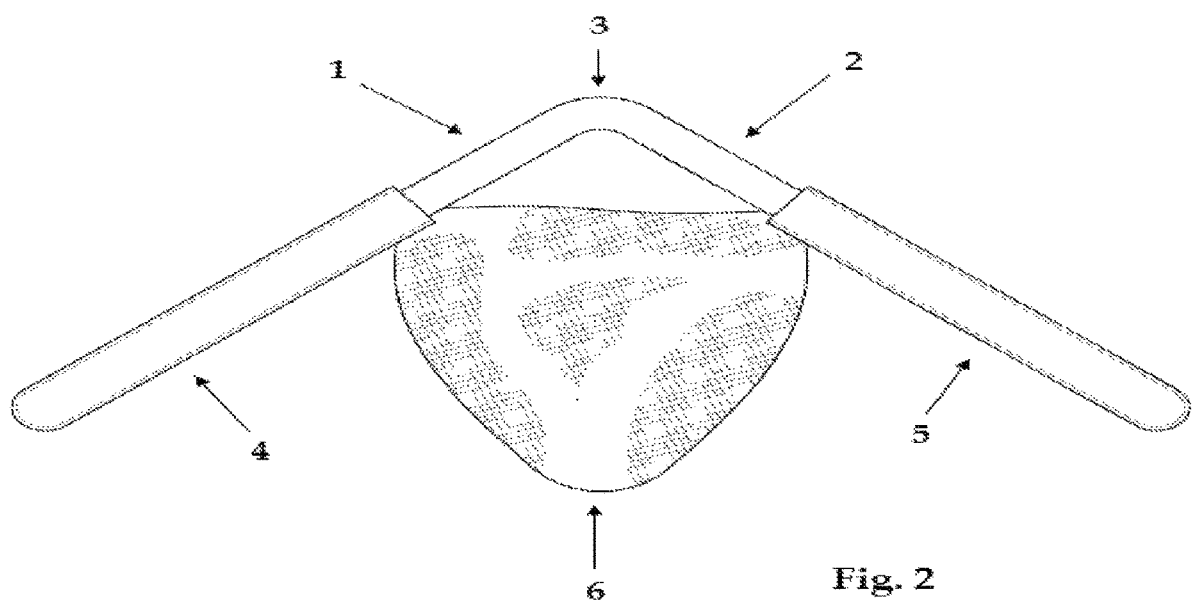
FIG. 2 illustrates a side view of a disposable tongue scraper bent at an acute angle, according to an embodiment of the present invention.
Figure 3:
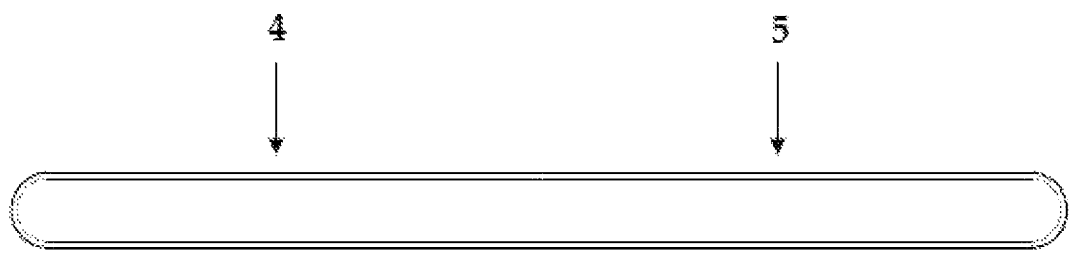
FIG. 3 illustrates a top view of a disposable tongue scraper before and after the scraping operation, according to an embodiment of the present invention.

Now referring to FIGS. 1, 2 & 3, various views of the disposable tongue scraper of the present invention are shown which comprise: a left scraper body (1) and a right scraper body (2), substantially form a curved shape after bending at an acute angle at a bending point (3) to enable it to scrape the coating formed on the tongue due to food debris, desquamated epithelial cells and bacteria; the bending point (3) in the middle of the scraper body (1, 2) at which the tongue scraper bends at an acute angle for scraping; a pair of left handle casing (4) and right handle casing (5) of any suitable material, attached with the scraper body (1, 2) to hold the tongue scraper while scraping, and also to cover the scraper body (1, 2) inside when not using; and a storage tissue net (6) attached to the bottom of the scraper body (1, 2), to store the scraped oral wastes and to absorb the oral fluids.

According to an embodiment of the present invention, a top view of the disposable tongue scraper is shown in FIG. 1, in which the tongue scraper is in an expanded position. The scraper body (1, 2) and the storage tissue net (6) are enclosed inside the handle casings (4, 5) before the scraping operation, as shown in FIG. 3. When a user grasps both ends of the handle casings (4, 5) and expands it out in opposite directions, the scraper body (1, 2) slide-out from inside, and also the storage tissue net (6) expands out in a circular motion as shown in FIG. 1. This is how the storage tissue net (6) looks before the user bends the tongue scraper at an acute angle to scrape the tongue.

According to another embodiment of the present invention, a side view of the disposable tongue scraper bent at an acute angle is shown in FIG. 2. After expanding out the handle casings (4, 5) of the tongue scraper as described in the abovementioned paragraph, the user can bend the scraper body (1, 2) at an acute angle which then substantially form a curved shape after bending at the bending point (3) to enable to scrape the coating formed on the tongue. Once the tongue scraper is bent at an acute angle, the storage tissue net (6) caves in as shown in FIG. 2, and allows the scraped oral wastes to dispose of it. The user then closes back the tongue scraper with the handle casings (4, 5) when finished, and disposes of the tongue scraper in a dustbin.

Further, the handle casings (4, 5) enclose the scraper body (1, 2) and the waste-filled storage tissue net (6) after scraping operation, simply by pushing the handle casings (4, 5) towards each other, as shown in FIG. 3.

The disposable tongue scraper of the present invention is highly advantageous over conventional tongue scrapers. The disposable tongue scraper of the present invention provides a facility to store the oral wastes and saliva wastes from the tongue when scraping; hence no need to dispose of the oral wastes and saliva wastes in the bathroom sinks. More importantly, the design of the tongue scraper is expandable and foldable so that the user can dispose of it by maintaining surrounding cleanliness.

Concerning the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

The invention has been explained about specific embodiment. It is inferred that the foregoing description is only illustrative of the present invention and it is not intended that the invention be limited or restrictive thereto. Many other specific embodiments of the present invention will be apparent to one skilled in the art from the foregoing disclosure. All substitution, alterations, and modification of the present invention that come within the scope of the following claims are to which the present invention is readily susceptible without departing from the spirit of the invention. The scope of the invention should therefore be determined not concerning the above description but should be determined concerning appended claims along with the full scope of equivalents to which such claims are entitled.

LIST OF REFERENCE NUMERALS

1 left scraper body
2 right scraper body

3 bending point
4 left handle casing
5 right handle casing
6 storage tissue net

The invention claimed is:

1. A disposable tongue scraper, comprising:
   a left scraper body and a right scraper body, which form a curved shape after the tongue scraper bends at an acute angle;
   a left handle casing and a right handle casing attached to the left and right scraper bodies respectively, to hold the tongue scraper while scraping;
   a storage tissue net attached to a bottom of the left and right scraper body bodies to store scraped oral wastes and to absorb oral fluids;
   wherein the left and right scraper bodies and the storage tissue net are enclosed inside the left and right handle casings, before scraping operation.

2. A disposable tongue scraper, comprising:
   a left scraper body and a right scraper body, which form a curved shape after the tongue scraper bends at an acute angle;
   a left handle casing and a right handle casing attached to the left and right scraper bodies respectively, to hold the tongue scraper while scraping;
   a storage tissue net attached to a bottom of the left and right scraper body bodies to store scraped oral wastes and to absorb oral fluids;
   wherein the left and right scraper bodies and the storage tissue net are enclosed inside the left and right handle casings, after scraping operation.

* * * * *